United States Patent
Elist

(10) Patent No.: US 6,537,204 B1
(45) Date of Patent: Mar. 25, 2003

(54) STRUCTURAL PENILE IMPLANT

(76) Inventor: James Elist, 9033 Wilshire Blvd., Suite 300, Beverly Hills, CA (US) 90211

( * ) Notice: Subject to any disclaimer, the term of this patent is extended or adjusted under 35 U.S.C. 154(b) by 0 days.

(21) Appl. No.: 10/014,740

(22) Filed: Dec. 10, 2001

(51) Int. Cl.⁷ .................................................. A61F 5/00
(52) U.S. Cl. ........................................................ 600/40
(58) Field of Search ............... 600/38–41; 128/DIG. 25

(56) References Cited

U.S. PATENT DOCUMENTS

| | | | |
|---|---|---|---|
| 1,383,944 A | * 7/1921 | Hart | 600/39 |
| 2,899,957 A | * 8/1959 | Briggs | 600/39 |
| 3,893,456 A | 7/1975 | Small et al. | |
| 3,987,789 A | 10/1976 | Timm et al. | |
| 4,204,530 A | 5/1980 | Finney | |
| 4,483,331 A | 11/1984 | Trick | |
| 4,523,584 A | * 6/1985 | Yachia et al. | 600/38 |
| 4,589,405 A | * 5/1986 | Hemmeter | 600/40 |
| 4,602,625 A | * 7/1986 | Yachia et al. | 600/40 |
| 4,669,456 A | 6/1987 | Masters | |
| 5,445,594 A | * 8/1995 | Elist | 600/38 |
| 5,512,033 A | 4/1996 | Westrum, Jr. et al. | |
| D376,011 S | 11/1996 | Nunokawa | |
| 5,669,870 A | * 9/1997 | Elist | 600/40 |
| 6,015,380 A | 1/2000 | Subrini | |

FOREIGN PATENT DOCUMENTS

WO    WO 86/01398    3/1986

* cited by examiner

*Primary Examiner*—Samuel G. Gilbert
(74) *Attorney, Agent, or Firm*—Gene Scott-Patent Law & Venture Group

(57) ABSTRACT

A penile implant apparatus has an arced, elongated body providing a wall thickness varying circumferentially from a maximum thickness at a top longitudinally directed surface, to a minimum thickness along a pair of bottom, longitudinally directed and spaced apart edges. The body may be constructed as a single integral form or as two mirror image related half portions which are joined during implantation. The wall thickness further varies longitudinally from the maximum thickness at a proximal circumferential edge to the minimum thickness at a distal circumferential edge. The apparatus is preferably made of silicone rubber, has a length and size enabling implantation subcutaneously and provides sufficient rigidity for enabling coitus.

14 Claims, 2 Drawing Sheets

STRUCTURAL PENILE IMPLANT

BACKGROUND OF THE INVENTION

1. Field of the Invention

This invention relates generally to surgical implants for the enhancement of appearance and operation of organs and more particularly to a penile implant enabling a damaged penis or penis function to be restored to full sexual function.

2. Description of Related Art

The following art defines the present state of this field:

Nunokawa, U.S. Des. 376,011 describes a synthetic vascular prosthesis design.

Small et al., U.S. Pat. No. 3,893,456 describes a prosthesis for implantation in the penis to provide a flaccid penis with rigidified dimensions of length and of width, and with the property of flexural stiffness. The prosthesis is used in pairs, each of which is a one-piece member that includes a composite rod having a dimension of axial length and, for the major proportion of its length, is composed of two physically distinct bodies which are integrally joined to each other, one of which is more resistant to bending and to compressive deformation than the other, and ap rong extending from said rod, said prong decreasing in lateral cross-section as it extends away from the rod. One of the bodies is stiffly flexible. In the preferred embodiment of the invention, the first of the bodies is a tube of solid material having an inner wall and an outer wall, the inner wall defining an axially extending cavity, the second body filling the cavity, the said first body being the one which is stiffly flexible. The second body is preferably made of a gel or of a foam.

Timm et al., U.S. Pat. No. 3,987,789 describes a prosthesis adapted to be implanted in the penis for simulating an erection is disclosed herein. The prosthesis includes an elongated, malleable rod portion which is housed within a generally tubular, physiologically inert plastic body. The malleable rod portion enables the prosthesis to be conformed to a variety of shapes by bending or twisting same. During intercourse the prosthesis will maintain the penis in an erectile state, and afterwards the penis may be positioned and maintained by the prosthesis in a convenient, comfortable position.

Finney, U.S. Pat. No. 4,204,530 describes an implantable sleeve for increasing the penile diameter including a flexible sheet of soft, physiologically acceptable implantable material, said sheet being of sufficient length when formed in the general shape of a cylindrical sleeve to extend from the glans penis to the base of the penis and of a width which is insufficient to completely encircle the, penis, but sufficient to cover the corpora cavernosa. The sheet preferably has edges which are rounded and tapered side edges. The sleeve also includes suturing strips on the inside wall of the sleeve adjacent the side edges of the sheet which facilitate the suturing of the sheet to the tunica albuginea. The sleeve further includes porous patches located on the interior of the inside wall of the sleeve into which fibroblasts from the underlying tissues can grow to further anchor the sleeve to the tunica albuginea. In the preferred embodiment, the sheet is of very soft, medical grade silicone elastomer, and suturing strips are of Dacron fabric and the porous patches are of Dacron fabric or fluff.

Trick, U.S. Pat. No. 4,483,331 describes an improved rod-type penile implant having a relatively stiff proximal portion for positioning inside the corpus cavernosum adjacent the pubis for supporting the implant, a longer relatively stiff distal portion for positioning in the corpus cavernosum of the pendulous penis and a hinge separating the distal and proximal portions, the improvement which comprises a distal portion including a reinforced inner core having a main body of relatively stiff material which is united to an outer tubular sleeve of fabric having a relatively high tensile strength so that the main body and fabric sleeve act together to increase the stiffness of the inner core.

Masters, U.S. Pat. No. 4,669,456 describes an implantable, positionable penile prosthesis which comprises an elastomeric rod and a metal wire coil coaxially imbedded within at least a portion of the rod. The coil has a radius, number of turns per unit length, and wire diameter which combines with the elastomeric rod for substantially retaining the position into which the prosthesis is bent and for inhibiting fatigue of the metal wire coil when the prosthesis is repeatedly bent for positioning.

Westrum, Jr. et al., U.S. Pat. No. 5,512,033 describes a malleable penile prosthesis adapted to be implanted in a corpus cavernosum of a penis comprising an elongated core which is bendable about its longitudinal axis with the capability of holding the configuration to which it is bent and is substantially rigid when in the unbent straight configuration, a sleeve of braided biocompatible material, having an inner surface and an outer surface, enveloping the core with the inner surface of the sleeve in contact with the core and the sleeve and core being accommodated within an outer tube of elastomeric material, which tube has a substantially rounded smooth outer surface and an inner surface having a profile formed of alternate grooves and ribs in a substantially helical arrangement. A method of forming a malleable prosthesis is also disclosed.

Subrini, U.S. Pat. No. 6,015,380 describes an extra cavernosal penile implant which can be used to increase penile volume. The implant includes two cheeks independent from one another which are adapted to cover the outer lateral sides of the corpus cavernosum without covering the upper and lower sides thereof. Each of the cheeks has a crescent-shaped or hemicylindrical vertical cross-section. Each cheek also includes a distal end which is adapted to conform to the anatomy of the sulcus of the glans and includes for this purpose an oblique planar end surface which slants from the distal end toward the proximal end of the implant in a direction from the outer surface to the inner surface of the implant which is designed to cover the corpus cavernosum.

Moreira de Azeredo, WO 86/01398 describes a penile rigidity prosthesis for the treatment of erectile impotence in men including at least one penile implant comprising an elongated malleable cylindrical body adapted to be surgically implanted in the corpus cavernosum of the penis; said body having a rounded front tip and an anatomical design at the end; the outer sheet of the cylinder is made of harder elastic material while the inner of considerably softer one; embedded in this material there is a core of twisted metal wires. In the variable size type the wires are fixed into a screw, allowing intermediate small cylinder extensions and a tail end to be screwed all together.

The prior art teaches the use of a subcutaneously implanted tube to rigidize the penis, but does not teach the use of certain contours that provide structural advantages. The present invention fulfills these needs and provides further related advantages as described in the following summary.

SUMMARY OF THE INVENTION

The present invention teaches certain benefits in construction and use which give rise to the objectives described below.

A penile implant apparatus comprising: an arced, elongated body providing a wall thickness varying circumferentially from a maximum thickness at a top longitudinally directed surface, to a minimum thickness along a pair of bottom, longitudinally directed and spaced apart edges. The wall thickness further varies longitudinally from the maximum thickness at a proximal circumferential edge to the minimum thickness at a distal circumferential edge. The apparatus is preferably made of silicone rubber, has a length and size enabling implantation subcutaneously within the human penis and provides sufficient rigidity for enabling coitus while still being flexible enough to be conveniently positioned when not involved in coitus.

A primary objective of the present invention is to provide an apparatus and method of use of such apparatus that provides advantages not taught by the prior art.

Another objective is to provide such an invention capable of providing rigidity to the human penis so as to enable coitus in a penis without the aid of normal erectile function.

A further objective is to provide such an invention capable of providing the necessary rigidity to the penis while providing an appropriate tapered appearance.

A still further objective is to provide such an invention capable of being cut to length to fit a wide range of human males.

A still further objective is to enable surgical implantation without removal of existing organ portions or related tissues.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above described drawing figures illustrate the invention in at least one of its preferred embodiments, which is further defined in detail in the following description.

Figure 1:
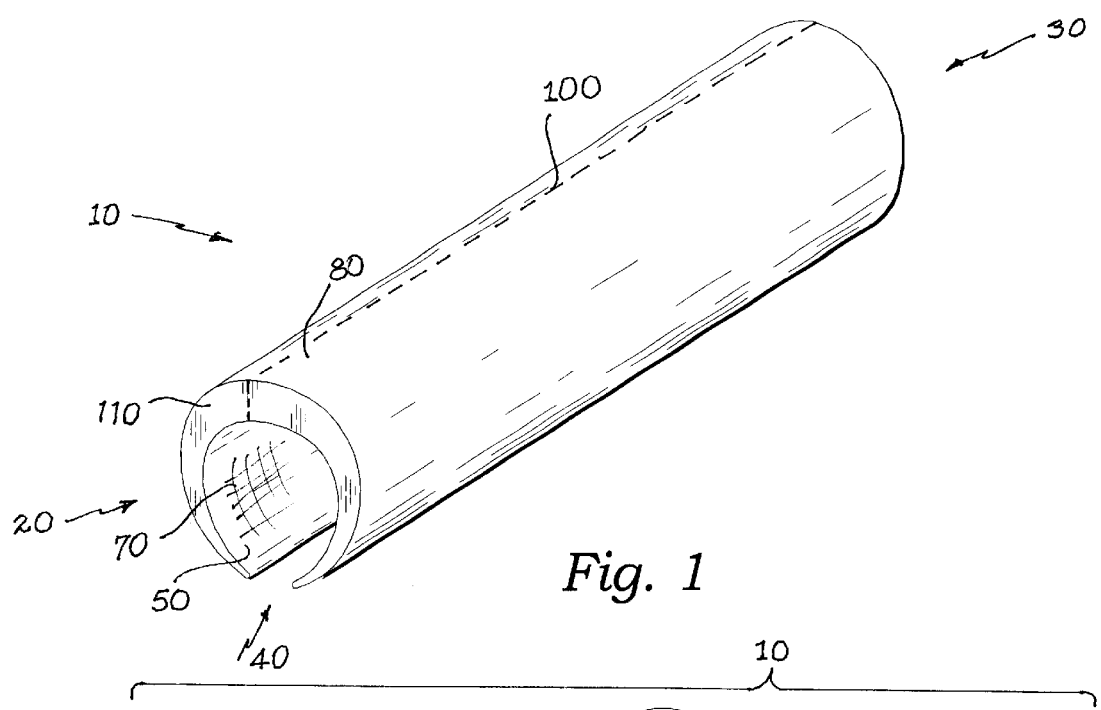
FIGS. 1 and 2 are perspective views of a first and a second preferred embodiments of the invention respectively.
Figure 2:
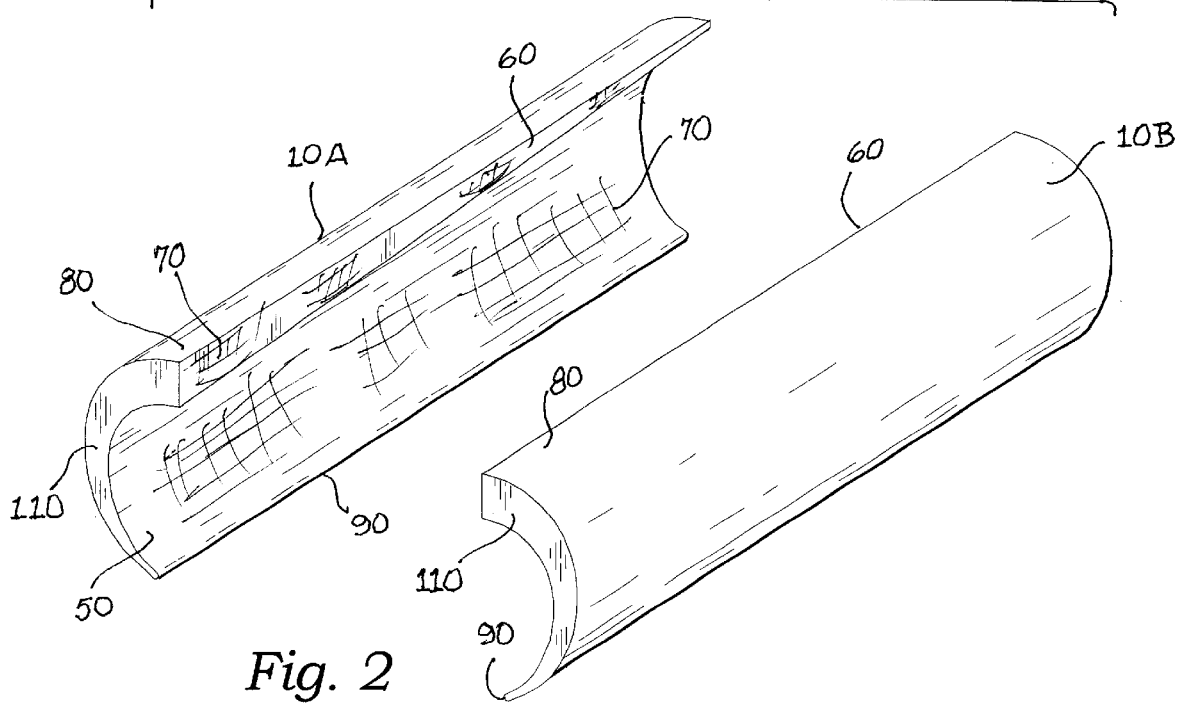
Figure 3:
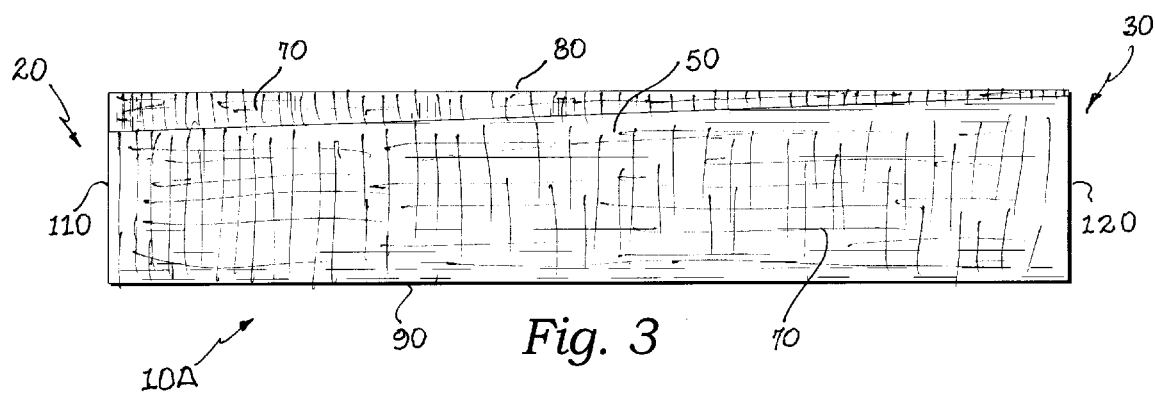
FIG. 3 is a side elevational view of the second embodiment thereof.

The invention is a penile implant apparatus comprising, a body 10 of a desired length and formed as a cylinder, open at its ends 20, 30 and open also along an underside longitudinal portion 40 extending the full length of the cylinder. The body 10 may be formed as a single integral part, as shown in FIG. 1, or as a pair of halves 10A, 10B, as shown in FIG. 2. In the latter case, the halves are mirror images of each other in form, and are joined when the apparatus is surgically implanted. The implantation process is taught in Finney, U.S. Pat. No. 4202530 which is hereby incorporated into the present application by reference. Thus, it is clear that the present apparatus is of a size, shape and has a wall thickness adapted for implantation within the human penis between the penile skin and the dorsum of the corpora cavernosa. The apparatus extends from the glans penis at its distal end 30, to the base of the penis at its proximal end 20.

An inside surface 50 of the apparatus as well as the abutting longitudinal edges 60 of the two halves have a silicon netting 70 imbedded as shown in the figures. This netting 70 is used for fastening sutures. The apparatus, when placed over the dorsum is anchored using sutures in fastening the netting to the Buck's fascia or tunica albuginea, or both.

Importantly, the apparatus; either the single integral embodiment of FIG. 1, or the joined dual halves of FIG. 2, provides a wall thickness that varies circumferentially from a maximum thickness along a top longitudinally directed surface 80, to a minimum thickness along a pair of spaced apart bottom longitudinally directed edges 90. It should be clear that FIG. 1 represents both the single integral body embodiment as well as the form taken when the two halves shown in FIG. 2 are joined. The joining line 100 would be as shown in FIG. 1. The wall thickness further varies longitudinally from the maximum thickness at a proximal circumferential edge 110 which defines the proximal end 20, to the minimum thickness at a distal circumferential edge 120 which defines the distal end 30. The bottom longitudinally directed edges 90 are spaced: apart as best shown in FIG. 1. Preferably the apparatus is constructed of silicone rubber or a similar material compatible with the human biosystem and is of a length and size adapted for the human penis. The material of construction is of such a rigidity as to enable the penis, so implanted, to enjoy the act of coitus without being aided by the normal stiffening associated with the erectile function of the penis.

The structural features of the present invention provide significant advantages over the prior art which is primarily defined by Finney. These structural features are enumerated as follows:

The thicker wall near the base of the penis provides an advantage in improved rigidity of the apparatus in terms of directing the penis outwardly in the appropriate direction for coitus. The thinner wall near glans penis allows for improved flexibility of the glans penis. The uniform taper from proximal 110 to distal 129 edges provides a more natural penile conformation, improved blood flow toward the glans penis and improved flexibility of the organ when not engaged in coitus. The Thicker wall at the top 80 of the apparatus provides greater structural strength where the highest compressive forces occur during coitus. The uniform taper from the top of the apparatus, around the sides, to the bottom provides improved flexibility of the penis and a more natural penile conformation. It also provides improved blood flow in general since the apparatus may be quite thin near the glans penis without loosing necessary rigidity. The important result of the conformation of the present invention is the use of the least material while achieving maximum rigidity and blood flow. The use of a netting 70 imbedded within the interior surface of the apparatus provides maximum flexibility as to placement of sutures. The use of the split halves 10A, 10B greatly facilitates implantation and also provides the opportunity to use asymmetrical halves as necessary for repair of damaged or misshaped organs. The space between the bottom longitudinal edges 90 allows the corpus spongeosum of the urethra to remain free of any pressure, as necessary.

Figures 4, 5:
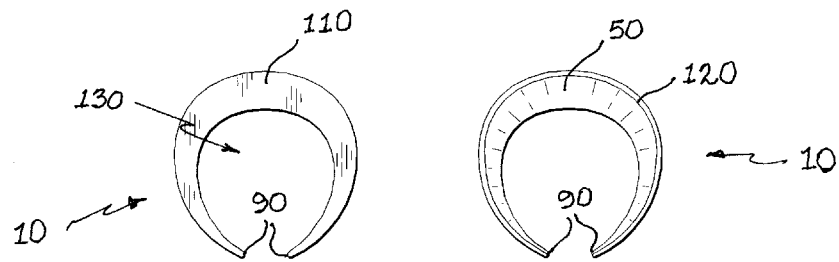
FIGS. 4 and 5 are front-end and rear-end views respectively of the first embodiment thereof.

Preferably, the elongated body defines an interior space 130, as shown in FIG. 4. This interior space 130 is preferably oblate with height greater than width and preferably has an aspect ratio of approximately 1.12. It has been discovered that this form provides for improved blood flow and fit to the natural tissue conformations of the human penis.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A penile implant apparatus comprising: a pair of arced, elongated portions, the portions being mirror images of each other; each of the portions providing a wall thickness varying circumferentially from a maximum thickness at a top longitudinally directed edge, to a minimum thickness along a bottom longitudinally directed edge; the wall thickness further varying longitudinally from a proximal circumferential edge having a thickness commensurate with said maximum thickness of the top longitudinally directed edge, to a distal circumferential edge having a thickness commensurate with said minimum thickness along said bottom longitudinally directed edge.

2. The apparatus of claim 1 wherein, with the top longitudinally directed edges of the portions in abutment, the pair of bottom longitudinally directed edges are spaced apart.

3. The apparatus of claim 1 wherein the apparatus is constructed of silicone rubber and further includes a silicon netting imbedded within.

4. The apparatus of claim 3 wherein the netting fully covers an interior surface of each of the elongated portions and the top longitudinally directed edge thereof.

5. The apparatus of claim 1 wherein the apparatus is of a length and size enabling implantation subcutaneously within a human penis.

6. The apparatus of claim 1 wherein the apparatus is of a rigidity for enabling coitus.

7. The apparatus of claim 1 wherein, with the top longitudinally directed edges of the portions in abutment, an interior space is defined; the interior space being oblate with height greater than width.

8. A penile implant apparatus comprising: an arced, elongated body providing a wall thickness varying circumferentially from a maximum thickness at a top longitudinally directed surface, to a minimum thickness along a pair of bottom, longitudinally directed and spaced apart edges; the wall thickness further varying longitudinally from the maximum thickness of the top longitudinally directed surface, at a proximal circumferential edge to the minimum thickness of the pair of bottom edges, at a distal circumferential edge.

9. The apparatus of claim 8 wherein the apparatus is constructed of silicone rubber and further includes a silicon netting imbedded within.

10. The apparatus of claim 9 wherein the netting fully covers an interior surface of the elongated body.

11. The apparatus of claim 8 wherein the apparatus is of a length and size enabling implantation subcutaneously within the human penis.

12. The apparatus of claim 8 wherein the apparatus is of a rigidity for enabling coitus.

13. The apparatus of claim 8 wherein the elongated body defines an interior space; the interior space being oblate with height greater than width.

14. The apparatus of claim 13 wherein an aspect ratio of the interior space is approximately 1.12.

* * * * *